United States Patent [19]

Neville, Jr. et al.

[11] Patent Number: 4,520,226

[45] Date of Patent: May 28, 1985

[54] TREATMENT OF GRAFT VERSUS HOST DISEASE USING A MIXTURE OF T-LYMPHOCYTE SPECIFIC MONOCLONAL ANTIBODY: RICIN CONJUGATES

[75] Inventors: David M. Neville, Jr., Bethesda, Md.; Richard J. Youle, Washington, D.C.

[73] Assignee: The United States of America as represented by the Department of Health and Human Services, Washington, D.C.

[21] Appl. No.: 456,401

[22] Filed: Jan. 7, 1983

Related U.S. Application Data

[63] Continuation-in-part of Ser. No. 399,257, Jul. 19, 1982.

[51] Int. Cl.$^3$ .................... A61K 39/395; C12N 15/00
[52] U.S. Cl. ..................................... 424/85; 436/548; 435/2; 435/68; 435/172.2; 435/240; 435/259; 424/85; 514/8; 935/108
[58] Field of Search .................. 436/548; 435/68, 172, 435/240, 2, 259; 424/85, 177, 195; 935/104, 106, 108

[56] References Cited

U.S. PATENT DOCUMENTS

| | | | |
|---|---|---|---|
| 4,340,535 | 7/1982 | Voisin et al. | 260/112 B |
| 4,356,117 | 10/1982 | Neville et al. | 260/112 R |
| 4,359,457 | 11/1982 | Neville et al. | 424/85 |
| 4,363,758 | 12/1982 | Masutto et al. | 260/112 B |
| 4,368,149 | 12/1983 | Masutto et al. | 260/112 B |
| 4,397,843 | 8/1983 | Neville et al. | 424/177 |
| 4,414,148 | 11/1983 | Jansen et al. | 260/112 B |

FOREIGN PATENT DOCUMENTS 0074279  3/1983  European Pat. Off.
0063988  3/1982  France.

OTHER PUBLICATIONS

Howard, J. C. et al., Immunological Reviews, vol. 47, pp. 160–174, (1979).
Uotilla, M. et al., Journal of Immunological Methods, vol. 42, pp. 11–15, (1981).
Katus, H. A. et al., Molecular Immunology, vol. 19, pp. 451–455, (1982).
Ehrlich, P. H. et al., Journal of Immunology, vol. 128(6), (1982).
Royston, I. et al., J. Immunology, vol. 125, pp. 725–731, (1980).
Beverly, P. C. L. et al., European J. Immunology, vol. 11, pp. 329–334, (1981).
Burns, G. F. et al., J. Immunology, vol. 129, pp. 1451- , (1982).
LeBien, T. W. et al., J. Immunology, vol. 125, pp. 2208–2214, (1980).
Ortaldo, J. R. et al., J. Immunology, vol. 127, pp. 2401–2409, (1981).
Youle et al., Proc. Natl. Acad. Sci. USA, vol. 77(9), pp. 5483–5486, (1980).
Gilliland et al., P.N.A.S., USA, vol. 77(8), pp. 4539–4543, (1980).
Neville et al., Bioc. Soc. Transact., vol. 8(6), pp. 692–693, (1980).
Pau, B. et al., Chem. Abstr., vol. 94(17), #132084f, (1980).
Houston, L. L., Chem. Abstr., vol. 95(25), #214896g, (1981).

(List continued on next page.)

*Primary Examiner*—Ben R. Padgett
*Assistant Examiner*—M. Moskowitz
*Attorney, Agent, or Firm*—John S. Roberts, Jr.

[57] ABSTRACT

A reagent and the protocol for the treatment of Graft Versus Host Disease is disclosed. Monoclonal antibodies specific for T-lymphocytes in human donor bone marrow are covalently linked to separate ricin toxin, combined in a mixture to form a treatment reagent, and combined with bone marrow removed from a human donor. The bone marrow-reagent mixture is then infused into an irradiated recipient. This protocol virtually eliminates T-lymphocyte activity, the cause of Graft Versus Host Disease.

5 Claims, 3 Drawing Figures

OTHER PUBLICATIONS

Jansen et al., Chem. Abstr., vol. 95(15), #126185u, (1981).

Neville, D. M. et al., Chem. Abstr., vol. 95(17), #145343k, (1981).

Oeltmann, T. N. et al., Arch. Bioc. Biop., vol. 209(2), pp. 362-370, (1981).

Blythman, H. E. et al., Nature, vol. 290, pp. 145-146, (3-1981).

Vallera, D. A. et al., J. Exper. Med., vol. 155, pp. 949-954, (3-1982).

Youle, R. J. et al., J. Biol. Chem., vol. 257(4), pp. 1598-1601, (2-1982).

Hiroshi, M. et al., Gann, vol. 71(6), pp. 766-774, (1980).

Trowbridge, I. et al., Nature, vol. 294(5837), pp. 171-173, (11∝1981).

Krolick, K. A. et al., Proc. Natl. Acad. Sci., vol. 77(9), pp. 5419-5423, (1980).

Jansen, F. K. et al., vol. 96, p. 584, #1409 19p, Columbus, OH, (1982).

Vittetta, E. S. et al., Leukemia Markers Conf. Proc., pp. 381-395, (1981).

FIG. 1

% CONTROL (T CELL ACTIVITY OR STEM CELL COLONIES)

TA1-RICIN Conc. (ng/ml)

CFU-G

MLR

TREATMENT OF GRAFT VERSUS HOST DISEASE USING A MIXTURE OF T-LYMPHOCYTE SPECIFIC MONOCLONAL ANTIBODY: RICIN CONJUGATES

This application is a continuation-in-part application of Ser. No. 399,257, filed July 19, 1982.

PRIOR ART STATEMENT

Vallera, Daniel A., Richard J. Youle, David M. Neville, Jr., and John M. Kersey, *Journal of Experimental Medicine*, Vol. 155, pp. 949–954, March 1982.

U.S. Pat. No. 4,359,457 to Neville and Youle teaches the use of Thy 1.2 monoclonal antibody linked to intact ricin toxin as a murine lymphoma cytotoxic reagent.

Ser. No. 350,222, filed Feb. 19, 1982 to Neville and Youle teaches the use of Thy 1.1 monoclonal antibody linked to ricin toxin A chain as a cytotoxic reagent active against AKR murine thymocytes.

Ser. No. 350,223, filed Feb. 19, 1982 to Neville and Youle teaches the use of Thy 1.2 monoclonal antibody linked to ricin toxin in the treatment of graft versus host disease in animals.

Ser. No. 339,257, filed July 19, 1982 to Neville and Youle teaches the use of TA-1 monoclonal antibody linked to ricin toxin in the treatment of graft versus host disease in humans.

UTILITY STATEMENT

This invention represents an improved protocol in the treatment of graft versus host disease in humans. A three part mixture of monoclonal antibodies linked to ricin toxin show superior effectiveness in the elimination of cells which express the T-lymphocyte antigen. The reagent is useful in the treatment of any condition requiring bone marrow transplantation. This reagent is particularly useful in the treatment of aplastic anemia or leukemia patients who receive bone marrow transplants.

DESCRIPTION OF THE FIGURES

FIG. 1

Human bone marrow and peripheral blood mononuclear cells are treated with varying concentrations of TA-1-ricin plus lactose. Stem cell activity in terms of colony formation is monitored by the CFU-GEMM assay. T cell activity is monitored by the MLR assay. Data points are means of 7–10 separate experiments on separate individuals and hatching indicates ±1 standard deviation. In spite of large standard deviations, T cell activity is reduced by the reagent at concentrations which have little effect on stem cell activity. However, in some cases even at 1000 ng/ml not all measurable T cell activity is eliminated.

FIG. 2

Human peripheral blood mononuclear cells are treated with varying concentrations of the TA-1-ricin, UCHT1-ricin, and T101-ricin and an equal part mixture of all three (shown by the heavy lines). T cell activity is measured by the MLR assay. Individual and mixture assays are all performed on the same day with the same donor and responder cells. Data are averages of 4 separate experiments. The mixture of conjugates is superior to any of the single conjugates in eliminating T cell activity.

FIG. 3

Human peripheral blood mononuclear cells are treated with varying concentrations of the TA-1-ricin, UCHT1-ricin, and T101-ricin and an equal part mixture of all three (shown by the heavy lines). T cell activity is measured by the PHA assay. The inhibition of PHA response, plotted on a log scale, deviates from a single hit killing curve for each of the individual conjugates at 300 ng/ml. This indicates that there is a resistant population seen at 300 ng/ml. Likely causes of resistance at high doses are receptor saturation or a subset of cells containing only one or two of the antigenic determinants to which TA-1, T101, and UCHT1 are directed against. The mixture, heavy lines, maintains a log linear dose response to 300 ng/ml and provides superior cell killing ability.

GENERAL BACKGROUND

Figure 2:
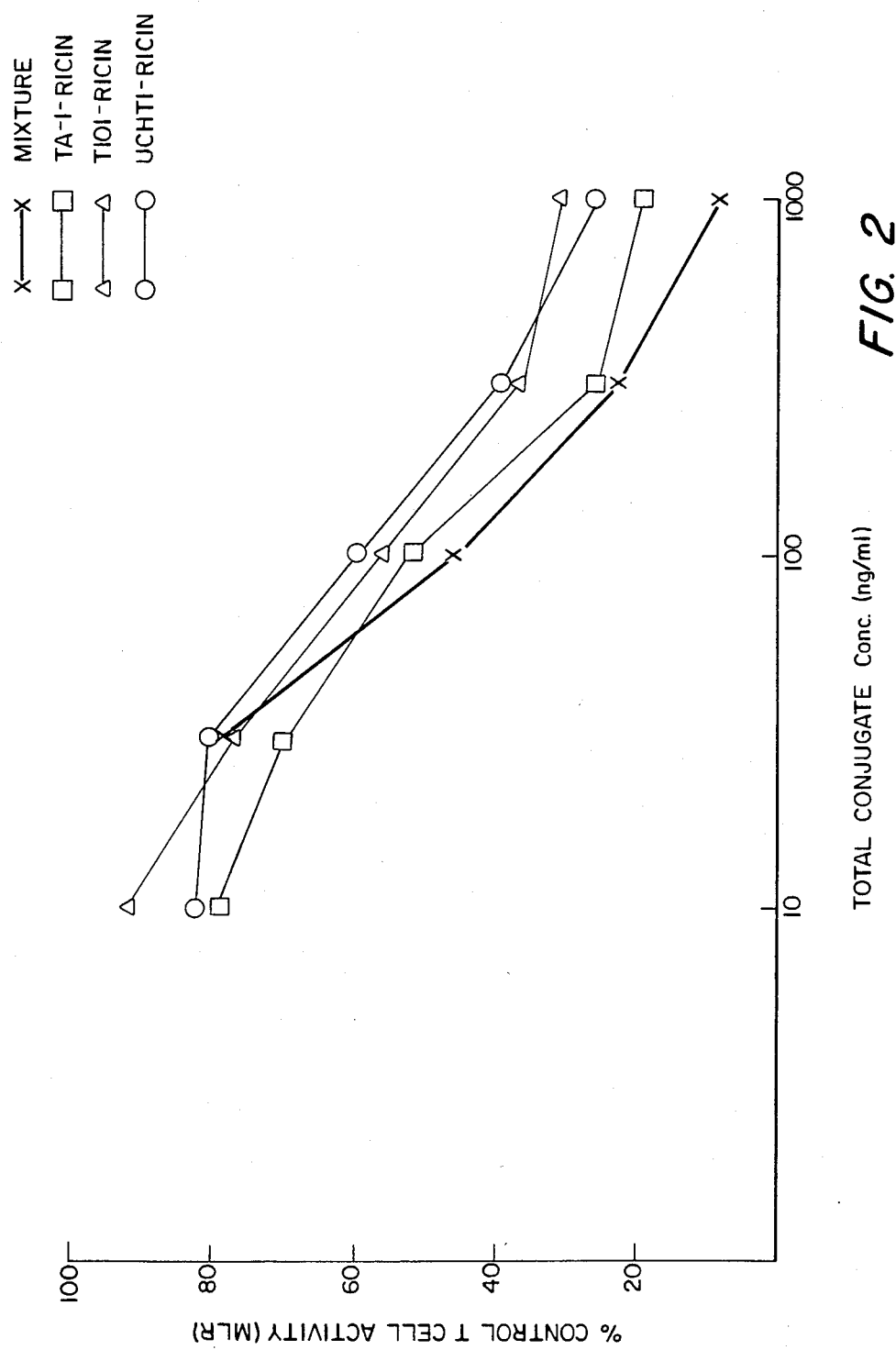

This application is a continuation-in-part application of Ser. No. 399,257, filed July 19, 1982, and represents an improvement in the protocol disclosed in the parent application. Ser. No. 399,257 teaches that T cell activity from peripheral blood which contaminates human bone marrow transplants can be largely eliminated by prior treatment with the monoclonal antibody-ricin conjugate TA-1-ricin plus lactose, under conditions that fail to damage the bone marrow stem cells necessary to repopulate the recipient's marrow. The present invention teaches the use of a mixture of three different anti-T cell mononclonal antibody ricin conjugates, preferably mixed in equal proportions. (See FIG. 2 for the results of a comparative study of various concentrations of the individual hybrids). This mixture is surprisingly far more effective in the elimination of T-cell activity while at the same time retaining the same total concentration of antibody ricin as is used in the single conjugate protocol.

In the context of treating human donor bone marrow cells, T-cells in the donor marrow react against the host cells and cause graft versus host disease. T-cell activity, that is, the severity of graft versus host disease following transplantation, is judged in humans by examining the T-cell stimulation by the mixed lymphocyte reaction between donor and recipient cells. Even though the TA1-ricin treatment of the parent application has proven effective, individual variation occurs due to either day-to-day variations of an unknown nature or the patient-to-patient variations (see, for example, the wide=1 standard deviation in FIG. 1). By mixing together three different anti-T-cell monoclonal antibody ricin conjugates in equal amounts, the ability of the mixture of eliminate T-cell activity is greatly enhanced. It is believed that some of the T-cells carry only one of the determinants necessary to bind the antibody. The mixture of three reagents has proven the most effective treatment possible.

SPECIFIC DESCRIPTION

In the synthesis of anti-human-T-cell-ricin hybrid, anti-human-T-cell monoclonal IgG (TA-1) is covalently linked to ricin. TA-1 antibody, commercially available from Hybritech, LaJolla, Calif. 0.25 ml at 2.6 mg/ml in 20 mM Tris-Cl pH 7.6 is mixed with 25λ of 1 M DTT and incubated at room temperature for 30 min. The DTT is then removed by G25F gel filtration. Ricin D 0.48 ml at 10.6 mg/ml is mixed with 17λ of MBS solution (1.5 mg of m-Maleimidobenzoyl-N-hydroxysuccinimide ester in 0.4 ml dimethyl formamide) and incubated 30 min. at room temperature. The DTT free TA-1 and MBS-ricin are then mixed and incubated 3 hrs. at room temperature. Then 20λ of 0.2 M N-ethylmaleimide is added and the hybrid is purified as previously described (Youle, R. J. and D. M. Neville, Jr., *Proc. Natl. Academy Sci.*, USA, Vol. 77, pp 5483–5486, 1980.

In the synthesis of T101-ricin hybrid, anti-human-T-cell monoclonal T101 is covalently linked to ricin. Antibody T101 is commercially available from Hybritech, La Jolla, Calif. T101 antibody, 0.25 ml at 2.6 mg/ml in 20 mM Tris-Cl pH 7.6, is mixed with 25λ of 0.1 M DTT and incubated at room temperature for 30 min. The DTT is then removed by G25F gel filtration. Ricin D, 0.24 ml at 10.6 mg/ml, is mixed with 8.0λ of MBS solution (1.5 mg of m-Maleimidobenzoyl-N-hydroxy-succinimide ester in 0.4 ml dimethyl formamide) and incubated 30 min. at room temperature. The DTT free T101 and MBS-ricin are then mixed and incubated 3 hrs. at room temperature. Then 20λ of 0.2 M N-ethylmaleimide is added and the hybrid is purified as previously described (Youle, R. J. and D. M. Neville, Jr., *Proc. Natl. Academy Sci.*, USA, Vol. 77, pp. 5483–5486, 1980.

The third conjugate in the mixture, UCHT1-ricin, is synthesized by the same method used to synthesize TA-1-ricin. UCHT1 monoclonal antibody was made available by Dr. Peter Beverley. A monoclonal antibody, OKT3 with the same specificity and similar affinity as UCHT1, may be substituted for UCHT1 and is commercially available from Ortho Pharmaceuticals.

The protocol used for the actual treatment of human donor bone marrow is as follows: the bone marrow is removed from the human donor, treated in vitro with a mixture of equal parts of TA-1-ricin, T101-ricin, and UCHT1-ricin under excess extracellular lactose conditions, and then infused into the irradiated recipient.

EXAMPLE

Each hybrid, TA-1-ricin, T101-ricin, and UCHT1-ricin, were assayed for their effect on human T-cells and human stem cells. In vitro, the hybrids eliminated T-cells at concentrations 50-fold lower than concentrations to kill stem cells (see FIG. 1).

Procedure:

1. Add a mixture of 333 mg/ml (final concentration) of each of TA-1-ricin, T101-ricin and UCHT1-ricin to 40 cc of 2% human serum albumin, 100 mM lactose, RPMI medium containing $10^7$ /ml density gradient centrifugation purified human nucleated bone marrow cells in 50 cc conical polystyrene tubes.

2. Peripheral blood density gradient purified mononuclear cells are treated in an identical manner and both sets are incubated for 2 hrs at 37° in a $CO_2$ incubator with the pH controlled at 7.35.

Figure 3:
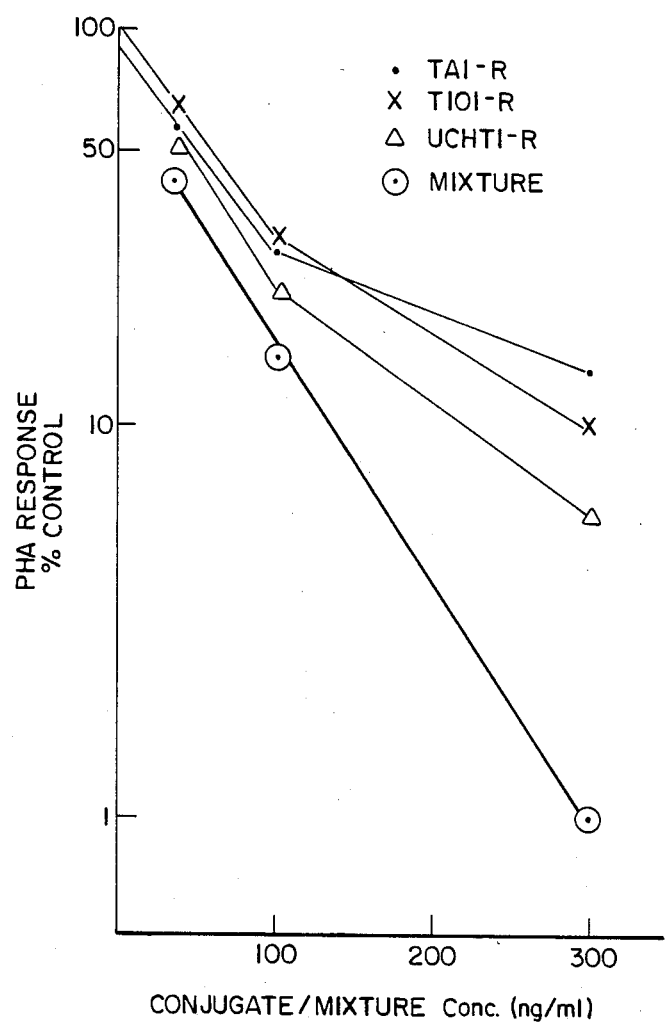

3. After incubation, the cells are washed 2× with PBS containing 1% HA+15 mM lactose and used as follows:
   a. The majority of the bone marrow cells are infused into an irradiated recipient at a dose of $2 \times 10^8$ cells/Kg.
   b. An aliquote of bone marrow cells are checked for viability in an in vitro clonogenic assay (CFU-GEMM).
   c. The peripheral blood mononuclear cells are assayed for elimination of T cell activity (see FIG. 2 and FIG. 3 for this result).

We claim:

1. A composition for the treatment of graft versus host disease in humans consisting essentially of a mixture of equal parts of conjugate molecules TA-1:ricin, T101:ricin, and UCHT1:ricin, said conjugate molecules consisting of ricin bonded to a monoclonal antibody, TA:1, T101 and UCHT1, respectively, said monoclonal antibody having binding specificity for a thymic lymphocyte antigenic site.

2. A method for the treatment of graft versus host disease in humans consisting essentially of covalently bonding antibodies exhibiting binding specificity for human bone marrow T-cells to ricin toxin in order to form three human T-cell specific cytotoxic hybrids; mixing said three hybrids in equal parts to form a reagent; incubating in vitro said reagent with human donor bone marrow cells obtained from a human donor in the presence of lactose, washing said bone marrow cells with PBS containing 1% HA and 15 mM lactose to remove any unbound conjugates; and injecting washed bone marrow cells incubated with said reagent into irradiated recipients.

3. The method of claim 2 wherein the human T-cell specific cytotoxic hybrids are TA-1-ricin, T101-ricin, and UCHT1-ricin.

4. The method of claim 2 in which the mixture is formed by combining equal amounts of TA-1-ricin, T101-ricin, and UCHT1-ricin.

5. A method for eliminating T-cells from human bone marrow grafts consisting essentially of separately covalently bonding monoclonal antibodies TA-1, T101, and UCHT1 to ricin toxins to form three human T-cell specific cytotoxic hybrids, forming a mixture by combining equal amounts of each hybrid, and incubating under standard biological conditions said mixture with human bone marrow cells in the presence of a suitable amount of lactose.

* * * * *

UNITED STATES PATENT AND TRADEMARK OFFICE
CERTIFICATE OF CORRECTION

PATENT NO. : 4,520,226

DATED : May 28, 1985

INVENTOR(S) : David M. Neville Jr., et al.

It is certified that error appears in the above-identified patent and that said Letters Patent is hereby corrected as shown below:

The term of this patent subsequent to February 19, 2002, has been disclaimed.

Signed and Sealed this

Tenth Day of September 1985

[SEAL]

Attest:

DONALD J. QUIGG

*Attesting Officer*   *Acting Commissioner of Patents and Trademarks - Designate*